(12) United States Patent
Zhou et al.

(10) Patent No.: US 7,923,505 B2
(45) Date of Patent: *Apr. 12, 2011

(54) HIGH-VISCOSITY ELASTOMERIC ADHESIVE COMPOSITION

(75) Inventors: Peiguang Zhou, Appleton, WI (US); Gregory K. Hall, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 683 days.

This patent is subject to a terminal disclaimer.

(21) Appl. No.: 11/938,928

(22) Filed: Nov. 13, 2007

(65) Prior Publication Data

US 2008/0064808 A1 Mar. 13, 2008

Related U.S. Application Data

(60) Division of application No. 10/701,259, filed on Nov. 4, 2003, now Pat. No. 7,316,842, which is a continuation-in-part of application No. 10/187,761, filed on Jul. 2, 2002, now Pat. No. 7,316,840.

(51) Int. Cl.
*C08L 9/00* (2006.01)

(52) U.S. Cl. ............ 524/571; 524/77; 524/78; 524/270; 524/574; 524/575

(58) Field of Classification Search .................... None
See application file for complete search history.

(56) References Cited

U.S. PATENT DOCUMENTS

| | | | |
|---|---|---|---|
| 2,206,761 A | 7/1940 | Berastein |
| 2,266,761 A | 12/1941 | Jackson, Jr. et al. |
| 2,357,392 A | 9/1944 | Francis, Jr. |
| 2,464,301 A | 3/1949 | Francis, Jr. |
| 2,483,405 A | 10/1949 | Francis, Jr. |
| 2,957,512 A | 10/1960 | Wade et al. |
| 2,957,852 A | 10/1960 | Frankenburg et al. |
| 3,186,893 A | 6/1965 | Mercer |
| 3,338,992 A | 8/1967 | Kinney |
| 3,341,394 A | 9/1967 | Kinney |
| 3,371,668 A | 3/1968 | Johnson |
| 3,391,048 A | 7/1968 | Dyer et al. |
| 3,439,085 A | 4/1969 | Hartmann |
| 3,449,187 A | 6/1969 | Bobkowicz |
| 3,468,748 A | 9/1969 | Bassett |
| 3,489,148 A | 1/1970 | Duncan et al. |
| 3,502,538 A | 3/1970 | Petersen |
| 3,502,763 A | 3/1970 | Hartmann |
| 3,542,615 A | 11/1970 | Dobo et al. |
| 3,575,782 A | 4/1971 | Hansen |
| 3,616,129 A | 10/1971 | Sager |
| 3,629,047 A | 12/1971 | Davison |
| 3,669,823 A | 6/1972 | Wood |
| 3,673,026 A | 6/1972 | Brown |
| 3,676,242 A | 7/1972 | Prentice |
| 3,689,342 A | 9/1972 | Vogt et al. |
| 3,692,618 A | 9/1972 | Dorschner et al. |
| 3,752,613 A | 8/1973 | Vogt et al. |
| 3,773,590 A | 11/1973 | Morgan |
| 3,802,817 A | 4/1974 | Matsuki et al. |
| 3,806,289 A | 4/1974 | Schwarz |
| 3,836,416 A | 9/1974 | Ropiequet |
| 3,838,692 A | 10/1974 | Levesque |
| 3,849,241 A | 11/1974 | Butin et al. |
| 3,855,046 A | 12/1974 | Hansen et al. |
| 3,857,144 A | 12/1974 | Bustin |
| 3,860,003 A | 1/1975 | Buell |
| 3,890,184 A | 6/1975 | Morgan |
| 3,904,465 A | 9/1975 | Haase et al. |
| 3,912,567 A | 10/1975 | Schwartz |
| 3,917,448 A | 11/1975 | Wood |
| 3,932,328 A | 1/1976 | Korpman |
| 3,949,128 A | 4/1976 | Ostermeier |
| 3,949,130 A | 4/1976 | Sabee et al. |
| 3,973,063 A | 8/1976 | Clayton |
| 3,978,185 A | 8/1976 | Buntin et al. |
| 3,979,050 A | 9/1976 | Cilia |
| 4,013,816 A | 3/1977 | Sabee et al. |
| 4,028,292 A | 6/1977 | Korpman |
| 4,038,346 A | 7/1977 | Feeney |
| 4,041,203 A | 8/1977 | Brock et al. |
| 4,080,348 A | 3/1978 | Korpman |
| 4,090,385 A | 5/1978 | Packard |
| 4,100,324 A | 7/1978 | Anderson et al. |

(Continued)

FOREIGN PATENT DOCUMENTS

CA 2 165 486 6/1996

(Continued)

OTHER PUBLICATIONS

Product data sheet for Escorez 1315 (no date).*

*Primary Examiner* — Marc S Zimmer

(74) *Attorney, Agent, or Firm* — Dority & Manning, P.A.

(57) ABSTRACT

High-viscosity elastomeric adhesive compositions including a high softening point tackifier resin in combination with a base polymer can be used to create elastomeric composite laminates having effective adhesion and elastic properties. The elastomeric adhesive compositions suitably have a viscosity between about 100,000 and about 500,000 cps at between about 300 degrees Fahrenheit (149 degrees Celsius) and about 350 degrees Fahrenheit (177 degrees Celsius). Facing layers, such as nonwoven webs, films, elastic strands, fastening material, absorbent material, and the like, can be laminated to one or both surfaces of the elastomeric compositions to form elastomeric composite laminates. A method of making such compositions and laminates involves forming the compositions into elastomeric adhesive films and/or strands.

19 Claims, 5 Drawing Sheets

U.S. PATENT DOCUMENTS

| | | | |
|---|---|---|---|
| 4,107,364 A | 8/1978 | Sisson | |
| 4,135,037 A | 1/1979 | Udipi et al. | |
| 4,148,676 A | 4/1979 | Paquette et al. | |
| 4,209,563 A | 6/1980 | Sisson | |
| 4,211,807 A | 7/1980 | Yazawa et al. | |
| 4,239,578 A | 12/1980 | Gore | |
| 4,241,123 A | 12/1980 | Shih | |
| 4,248,652 A | 2/1981 | Civardi et al. | |
| 4,259,220 A | 3/1981 | Bunnelle et al. | |
| 4,285,998 A | 8/1981 | Thibodeau | |
| 4,300,562 A | 11/1981 | Pieniak | |
| 4,302,495 A | 11/1981 | Marra | |
| 4,303,571 A | 12/1981 | Jansen et al. | |
| 4,304,234 A | 12/1981 | Hartmann | |
| 4,310,594 A | 1/1982 | Yamazaki et al. | |
| 4,319,572 A | 3/1982 | Widlund et al. | |
| 4,323,534 A | 4/1982 | DesMarais | |
| 4,333,782 A | 6/1982 | Pieniak | |
| 4,340,558 A | 7/1982 | Hendrickson | |
| 4,340,563 A | 7/1982 | Appel et al. | |
| 4,374,888 A | 2/1983 | Bornslaeger | |
| 4,375,446 A | 3/1983 | Fujii et al. | |
| 4,402,688 A | 9/1983 | Julemont | |
| 4,405,397 A | 9/1983 | Teed | |
| 4,413,623 A | 11/1983 | Pieniak | |
| 4,417,935 A | 11/1983 | Spencer | |
| 4,418,123 A | 11/1983 | Bunnelle et al. | |
| 4,438,167 A | 3/1984 | Schwarz | |
| 4,440,819 A | 4/1984 | Rosser et al. | |
| 4,490,427 A | 12/1984 | Grant et al. | |
| 4,496,417 A | 1/1985 | Haake et al. | |
| 4,507,163 A | 3/1985 | Menard | |
| 4,522,863 A | 6/1985 | Keck et al. | |
| 4,525,407 A | 6/1985 | Ness | |
| 4,543,099 A | 9/1985 | Bunnelle et al. | |
| 4,548,859 A | 10/1985 | Kline et al. | |
| 4,552,795 A | 11/1985 | Hansen et al. | |
| 4,555,811 A | 12/1985 | Shimalla | |
| 4,572,752 A | 2/1986 | Jensen et al. | |
| 4,586,199 A | 5/1986 | Birring | |
| D284,036 S | 6/1986 | Birring | |
| 4,606,964 A | 8/1986 | Wideman | |
| 4,618,384 A | 10/1986 | Sabee | |
| 4,626,305 A | 12/1986 | Suzuki et al. | |
| 4,636,419 A | 1/1987 | Madsen et al. | |
| 4,640,859 A | 2/1987 | Hansen et al. | |
| 4,644,045 A | 2/1987 | Fowells | |
| 4,652,487 A | 3/1987 | Morman | |
| 4,656,081 A | 4/1987 | Ando et al. | |
| 4,657,793 A | 4/1987 | Fisher | |
| 4,657,802 A | 4/1987 | Morman | |
| 4,661,389 A | 4/1987 | Mudge et al. | |
| 4,663,220 A | 5/1987 | Wisneski et al. | |
| 4,666,543 A | 5/1987 | Kawano | |
| 4,675,068 A | 6/1987 | Lundmark | |
| 4,683,877 A | 8/1987 | Ersfeld et al. | |
| 4,687,477 A | 8/1987 | Suzuki et al. | |
| 4,692,368 A | 9/1987 | Taylor et al. | |
| 4,692,371 A | 9/1987 | Morman et al. | |
| 4,698,242 A | 10/1987 | Salerno | |
| 4,704,116 A | 11/1987 | Enloe | |
| 4,718,901 A | 1/1988 | Singheimer | |
| 4,719,261 A | 1/1988 | Bunnelle et al. | |
| 4,720,415 A | 1/1988 | Vander Wielen et al. | |
| 4,725,468 A | 2/1988 | McIntyre | |
| 4,726,874 A | 2/1988 | Van Vliet | |
| 4,734,311 A | 3/1988 | Sokolowski | |
| 4,734,320 A | 3/1988 | Ohira et al. | |
| 4,734,447 A | 3/1988 | Hattori et al. | |
| 4,735,673 A | 4/1988 | Piron | |
| 4,756,942 A | 7/1988 | Aichele | |
| 4,761,198 A | 8/1988 | Salerno | |
| 4,762,582 A | 8/1988 | de Jonckheere | |
| 4,775,579 A | 10/1988 | Hagy et al. | |
| 4,777,080 A | 10/1988 | Harris, Jr. et al. | |
| 4,781,966 A | 11/1988 | Taylor | |
| 4,787,699 A | 11/1988 | Moulin | |
| 4,789,699 A | 12/1988 | Kieffer et al. | |
| 4,795,668 A | 1/1989 | Krueger et al. | |
| 4,798,603 A | 1/1989 | Meyer et al. | |
| 4,801,345 A | 1/1989 | Dussaud et al. | |
| 4,801,482 A | 1/1989 | Goggans et al. | |
| 4,803,117 A | 2/1989 | Daponte | |
| 4,804,577 A | 2/1989 | Hazelton et al. | |
| 4,818,464 A | 4/1989 | Lau | |
| 4,818,597 A | 4/1989 | DaPonte et al. | |
| 4,826,415 A | 5/1989 | Mende | |
| 4,842,666 A | 6/1989 | Werenicz | |
| 4,854,985 A | 8/1989 | Soderlund et al. | |
| 4,854,989 A | 8/1989 | Singheimer | |
| 4,863,779 A | 9/1989 | Daponte | |
| 4,867,735 A | 9/1989 | Wogelius | |
| 4,874,447 A | 10/1989 | Hazelton et al. | |
| 4,879,170 A | 11/1989 | Radwanski et al. | |
| 4,883,482 A | 11/1989 | Gandrez et al. | |
| 4,883,549 A | 11/1989 | Frost et al. | |
| 4,891,258 A | 1/1990 | Fahrenkrug | |
| 4,892,536 A | 1/1990 | DesMarais et al. | |
| 4,892,903 A | 1/1990 | Himes | |
| 4,900,619 A | 2/1990 | Ostrowski et al. | |
| 4,906,507 A | 3/1990 | Grynaeus et al. | |
| 4,908,247 A | 3/1990 | Baird et al. | |
| 4,908,253 A | 3/1990 | Rasmussen | |
| 4,910,064 A | 3/1990 | Sabee | |
| 4,917,696 A | 4/1990 | De Jonckheere | |
| 4,917,746 A | 4/1990 | Kons et al. | |
| 4,929,492 A | 5/1990 | Carey, Jr. et al. | |
| 4,935,021 A | 6/1990 | Huffman et al. | |
| 4,938,821 A | 7/1990 | Soderlund et al. | |
| 4,939,016 A | 7/1990 | Radwanski et al. | |
| 4,940,464 A | 7/1990 | Van Gompel et al. | |
| 4,949,668 A | 8/1990 | Heindel et al. | |
| 4,965,122 A | 10/1990 | Morman | |
| 4,968,313 A | 11/1990 | Sabee | |
| 4,970,259 A | 11/1990 | Mitchell et al. | |
| 4,977,011 A | 12/1990 | Smith | |
| 4,981,747 A | 1/1991 | Morman | |
| 4,984,584 A | 1/1991 | Hansen et al. | |
| 4,994,508 A | 2/1991 | Shiraki et al. | |
| 4,995,928 A | 2/1991 | Sabee | |
| 4,998,929 A | 3/1991 | Bjorksund et al. | |
| 5,000,806 A | 3/1991 | Merkatoris et al. | |
| 5,002,815 A | 3/1991 | Yamanaka et al. | |
| 5,005,215 A | 4/1991 | McIlquham | |
| 5,013,785 A | 5/1991 | Mizui | |
| 5,028,646 A | 7/1991 | Miller et al. | |
| 5,032,120 A | 7/1991 | Freeland et al. | |
| 5,034,008 A | 7/1991 | Breitkopf | |
| 5,045,133 A | 9/1991 | DaPonte et al. | |
| 5,057,368 A | 10/1991 | Largman et al. | |
| 5,060,349 A | 10/1991 | Walton et al. | |
| 5,069,970 A | 12/1991 | Largman et al. | |
| 5,073,436 A | 12/1991 | Antonacci et al. | |
| 5,093,422 A | 3/1992 | Himes | |
| 5,096,532 A | 3/1992 | Neuwirth et al. | |
| 5,100,435 A | 3/1992 | Onwumere | |
| 5,108,820 A | 4/1992 | Kaneko et al. | |
| 5,110,403 A | 5/1992 | Ehlert | |
| 5,112,889 A | 5/1992 | Miller et al. | |
| 5,114,087 A | 5/1992 | Fisher et al. | |
| 5,116,662 A | 5/1992 | Morman | |
| 5,145,727 A | 9/1992 | Potts et al. | |
| 5,147,487 A | 9/1992 | Nomura et al. | |
| 5,149,741 A | 9/1992 | Alper et al. | |
| D331,627 S | 12/1992 | Igaue et al. | |
| 5,169,706 A | 12/1992 | Collier, IV et al. | |
| 5,169,712 A | 12/1992 | Tapp | |
| 5,176,668 A | 1/1993 | Bernardin | |
| 5,176,672 A | 1/1993 | Bruemmer et al. | |
| 5,178,931 A | 1/1993 | Perkins et al. | |
| 5,186,779 A | 2/1993 | Tubbs | |
| 5,188,885 A | 2/1993 | Timmons et al. | |
| 5,192,606 A | 3/1993 | Proxmire et al. | |
| 5,198,281 A | 3/1993 | Muzzy et al. | |

| | | | | | | |
|---|---|---|---|---|---|---|
| 5,200,246 | A | 4/1993 | Sabee | 5,531,850 | A | 7/1996 | Herrmann |
| 5,204,429 | A | 4/1993 | Kaminsky et al. | 5,534,330 | A | 7/1996 | Groshens |
| D335,707 | S | 5/1993 | Igaue et al. | 5,536,563 | A | 7/1996 | Shah et al. |
| 5,209,801 | A | 5/1993 | Smith | 5,540,796 | A | 7/1996 | Fries |
| 5,219,633 | A | 6/1993 | Sabee | 5,540,976 | A | 7/1996 | Shawver et al. |
| 5,226,992 | A | 7/1993 | Morman | 5,543,206 | A | 8/1996 | Austin et al. |
| 5,229,191 | A | 7/1993 | Austin | 5,545,158 | A | 8/1996 | Jessup |
| 5,232,777 | A | 8/1993 | Sipinen et al. | 5,545,285 | A | 8/1996 | Johnson |
| 5,236,430 | A | 8/1993 | Bridges | 5,549,964 | A | 8/1996 | Shohji et al. |
| 5,236,770 | A | 8/1993 | Assent et al. | 5,569,232 | A | 10/1996 | Roe et al. |
| 5,238,733 | A | 8/1993 | Joseph et al. | 5,575,783 | A | 11/1996 | Clear et al. |
| 5,246,433 | A | 9/1993 | Hasse et al. | 5,576,090 | A | 11/1996 | Suzuki |
| D340,283 | S | 10/1993 | Igaue et al. | 5,582,668 | A | 12/1996 | Kling |
| 5,252,170 | A | 10/1993 | Schaupp | 5,591,152 | A | 1/1997 | Buell et al. |
| 5,259,902 | A | 11/1993 | Muckenfuhs | 5,591,792 | A | 1/1997 | Hattori et al. |
| 5,260,126 | A | 11/1993 | Collier, IV et al. | 5,595,618 | A | 1/1997 | Fries et al. |
| 5,272,236 | A | 12/1993 | Lai et al. | 5,597,430 | A | 1/1997 | Rasche |
| 5,277,976 | A | 1/1994 | Hogle et al. | 5,612,118 | A | 3/1997 | Schleinz et al. |
| 5,278,272 | A | 1/1994 | Lai et al. | 5,614,276 | A | 3/1997 | Petsetakis |
| 5,288,791 | A | 2/1994 | Collier, IV et al. | 5,620,780 | A | 4/1997 | Krueger et al. |
| 5,290,842 | A | 3/1994 | Sasaki et al. | 5,624,740 | A | 4/1997 | Nakata |
| 5,296,080 | A | 3/1994 | Merkatoris et al. | 5,626,573 | A | 5/1997 | Igaue et al. |
| 5,304,599 | A | 4/1994 | Himes | 5,628,856 | A | 5/1997 | Dobrin et al. |
| 5,308,345 | A | 5/1994 | Herrin | 5,645,672 | A | 7/1997 | Dobrin |
| 5,312,500 | A | 5/1994 | Kurihara et al. | 5,652,041 | A | 7/1997 | Buerger et al. |
| 5,324,580 | A | 6/1994 | Allan et al. | 5,660,664 | A | 8/1997 | Herrmann |
| 5,332,613 | A | 7/1994 | Taylor et al. | 5,663,228 | A | 9/1997 | Sasaki et al. |
| 5,334,437 | A | 8/1994 | Zafiroglu | 5,669,897 | A | 9/1997 | Lavon et al. |
| 5,334,446 | A | 8/1994 | Quantrille et al. | 5,680,653 | A | 10/1997 | Mathis et al. |
| 5,336,545 | A | 8/1994 | Morman | 5,681,302 | A | 10/1997 | Melbye et al. |
| 5,336,552 | A | 8/1994 | Strack et al. | 5,683,787 | A | 11/1997 | Boich et al. |
| 5,342,469 | A | 8/1994 | Bodford et al. | 5,690,626 | A | 11/1997 | Suzuki et al. |
| 5,360,854 | A | 11/1994 | Bozich, Jr. | 5,691,034 | A | 11/1997 | Krueger et al. |
| 5,364,382 | A | 11/1994 | Latimer et al. | 5,693,038 | A | 12/1997 | Suzuki et al. |
| 5,366,793 | A | 11/1994 | Fitts, Jr. et al. | 5,695,849 | A | 12/1997 | Shawver et al. |
| 5,376,198 | A | 12/1994 | Fahrenkrug et al. | 5,702,378 | A | 12/1997 | Widlund et al. |
| 5,376,430 | A | 12/1994 | Swenson et al. | 5,707,709 | A | 1/1998 | Blake |
| 5,382,400 | A | 1/1995 | Pike et al. | 5,709,921 | A | 1/1998 | Shawver |
| 5,385,775 | A | 1/1995 | Wright | 5,720,838 | A | 2/1998 | Nakata |
| 5,389,173 | A | 2/1995 | Merkatoris et al. | 5,733,635 | A | 3/1998 | Terakawa et al. |
| 5,389,438 | A | 2/1995 | Miller et al. | 5,733,822 | A | 3/1998 | Gessner et al. |
| 5,393,599 | A | 2/1995 | Quantrille et al. | 5,735,839 | A | 4/1998 | Kawaguchi et al. |
| 5,399,219 | A | 3/1995 | Roessler et al. | 5,736,219 | A | 4/1998 | Suehr et al. |
| 5,399,627 | A | * 3/1995 | Diehl et al. .................. 525/314 | 5,746,731 | A | 5/1998 | Hisada |
| 5,405,682 | A | 4/1995 | Shawyer et al. | 5,749,865 | A | 5/1998 | Yamamoto et al. |
| 5,407,507 | A | 4/1995 | Ball | 5,749,866 | A | 5/1998 | Roe et al. |
| 5,411,618 | A | 5/1995 | Jocewicz, Jr. | 5,766,389 | A | 6/1998 | Brandon et al. |
| 5,413,654 | A | 5/1995 | Igaue et al. | 5,766,737 | A | 6/1998 | Willey et al. |
| 5,413,849 | A | 5/1995 | Austin et al. | 5,769,838 | A | 6/1998 | Buell et al. |
| 5,415,644 | A | 5/1995 | Enloe | 5,769,993 | A | 6/1998 | Baldauf |
| 5,415,649 | A | 5/1995 | Watanabe et al. | 5,772,649 | A | 6/1998 | Siudzinski |
| 5,415,925 | A | 5/1995 | Austin et al. | 5,773,373 | A | 6/1998 | Wynne et al. |
| 5,422,172 | A | 6/1995 | Wu | 5,773,374 | A | 6/1998 | Wood et al. |
| 5,425,987 | A | 6/1995 | Shawver et al. | 5,788,804 | A | 8/1998 | Horsting |
| 5,429,629 | A | 7/1995 | Latimer et al. | 5,789,065 | A | 8/1998 | Haffner et al. |
| 5,429,694 | A | 7/1995 | Herrmann | 5,789,328 | A | 8/1998 | Kurihara et al. |
| 5,429,856 | A | 7/1995 | Krueger et al. | 5,789,474 | A | 8/1998 | Lu et al. |
| 5,431,644 | A | 7/1995 | Sipinen et al. | 5,790,983 | A | 8/1998 | Rosch et al. |
| 5,431,991 | A | 7/1995 | Quantrille et al. | 5,800,903 | A | 9/1998 | Wood et al. |
| 5,447,462 | A | 9/1995 | Smith et al. | 5,804,021 | A | 9/1998 | Abuto et al. |
| 5,447,508 | A | 9/1995 | Numano et al. | 5,804,286 | A | 9/1998 | Quantrille et al. |
| 5,449,353 | A | 9/1995 | Watanabe et al. | 5,814,176 | A | 9/1998 | Proulx |
| 5,464,401 | A | 11/1995 | Hasse et al. | 5,817,087 | A | 10/1998 | Takabayashi et al. |
| 5,466,410 | A | 11/1995 | Hills | 5,818,719 | A | 10/1998 | Brandon et al. |
| 5,472,775 | A | 12/1995 | Obijeski et al. | 5,830,203 | A | 11/1998 | Suzuki et al. |
| 5,476,458 | A | 12/1995 | Glaug et al. | 5,834,089 | A | 11/1998 | Jones et al. |
| 5,476,563 | A | 12/1995 | Nakata | 5,836,931 | A | 11/1998 | Toyoda et al. |
| 5,484,645 | A | 1/1996 | Lickfield et al. | 5,836,932 | A | 11/1998 | Buell et al. |
| 5,486,166 | A | 1/1996 | Bishop et al. | 5,840,412 | A | 11/1998 | Wood et al. |
| 5,490,846 | A | 2/1996 | Ellis et al. | 5,840,633 | A | 11/1998 | Kurihara et al. |
| 5,496,298 | A | 3/1996 | Kuepper et al. | 5,846,232 | A | 12/1998 | Serbiak et al. |
| 5,498,468 | A | 3/1996 | Blaney | 5,849,001 | A | 12/1998 | Torimae et al. |
| 5,500,075 | A | 3/1996 | Herrmann | 5,856,387 | A | 1/1999 | Sasaki et al. |
| 5,501,679 | A | 3/1996 | Krueger et al. | 5,858,515 | A | 1/1999 | Stokes et al. |
| 5,509,915 | A | 4/1996 | Hanson et al. | 5,860,945 | A | 1/1999 | Cramer et al. |
| 5,514,470 | A | 5/1996 | Haffner et al. | 5,865,933 | A | 2/1999 | Morin et al. |
| 5,516,476 | A | 5/1996 | Haggard et al. | 5,876,392 | A | 3/1999 | Hisada |
| 5,523,146 | A | 6/1996 | Bodford et al. | 5,879,776 | A | 3/1999 | Nakata |
| 5,527,300 | A | 6/1996 | Sauer | 5,882,573 | A | 3/1999 | Kwok et al. |

| | | |
|---|---|---|
| 5,885,656 A | 3/1999 | Goldwasser |
| 5,885,686 A | 3/1999 | Cederblad et al. |
| 5,897,546 A | 4/1999 | Kido et al. |
| 5,899,895 A | 5/1999 | Robles et al. |
| 5,902,540 A | 5/1999 | Kwok |
| 5,904,298 A | 5/1999 | Kwok et al. |
| 5,916,206 A | 6/1999 | Otsubo et al. |
| 5,921,973 A | 7/1999 | Newkirk et al. |
| 5,930,139 A | 7/1999 | Chapdelaine et al. |
| 5,931,581 A | 8/1999 | Garberg et al. |
| 5,932,039 A | 8/1999 | Popp et al. |
| 5,938,648 A | 8/1999 | LaVon et al. |
| 5,941,865 A | 8/1999 | Otsubo et al. |
| D414,262 S | 9/1999 | Ashton et al. |
| 5,952,252 A | 9/1999 | Shawver et al. |
| 5,964,970 A | 10/1999 | Woolwine et al. |
| 5,964,973 A | 10/1999 | Heath et al. |
| 5,990,377 A | 11/1999 | Chen et al. |
| 5,993,433 A | 11/1999 | St. Louis et al. |
| 5,997,521 A | 12/1999 | Robles et al. |
| 6,004,306 A | 12/1999 | Robles et al. |
| 6,033,502 A | 3/2000 | Coenen et al. |
| 6,045,543 A | 4/2000 | Pozniak et al. |
| 6,048,326 A | 4/2000 | Davis et al. |
| 6,057,024 A | 5/2000 | Mleziva et al. |
| 6,066,369 A | 5/2000 | Schulz et al. |
| 6,087,550 A | 7/2000 | Anderson-Fischer et al. |
| 6,090,234 A | 7/2000 | Barone et al. |
| 6,092,002 A | 7/2000 | Kastman et al. |
| 6,093,663 A | 7/2000 | Ouellette et al. |
| 6,096,668 A | 8/2000 | Abuto et al. |
| 6,123,694 A | 9/2000 | Pieniak et al. |
| 6,132,410 A | 10/2000 | Van Gompel et al. |
| 6,149,637 A | 11/2000 | Allen et al. |
| 6,152,904 A | 11/2000 | Matthews et al. |
| 6,169,848 B1 | 1/2001 | Henry |
| 6,183,587 B1 | 2/2001 | McFall et al. |
| 6,183,847 B1 | 2/2001 | Goldwasser |
| 6,197,845 B1 | 3/2001 | Janssen et al. |
| 6,214,476 B1 | 4/2001 | Ikeda et al. |
| 6,217,690 B1 | 4/2001 | Rajala et al. |
| 6,231,557 B1 | 5/2001 | Krautkramer et al. |
| 6,238,379 B1 | 5/2001 | Keuhn, Jr. et al. |
| 6,245,050 B1 | 6/2001 | Odorzynski et al. |
| 6,245,168 B1 | 6/2001 | Coenen et al. |
| 6,260,211 B1 | 7/2001 | Rajala et al. |
| 6,279,807 B1 | 8/2001 | Crowley et al. |
| 6,290,979 B1 | 9/2001 | Roe et al. |
| 6,310,164 B1 | 10/2001 | Morizono et al. |
| 6,316,013 B1 | 11/2001 | Paul et al. |
| 6,316,687 B1 | 11/2001 | Davis et al. |
| 6,316,688 B1 | 11/2001 | Hammons et al. |
| 6,320,096 B1 | 11/2001 | Inoue et al. |
| 6,323,389 B1 | 11/2001 | Thomas et al. |
| 6,329,459 B1 | 12/2001 | Kang et al. |
| 6,340,236 B1 * | 1/2002 | Hisanaga ............... 362/267 |
| 6,364,863 B1 | 4/2002 | Yamamoto et al. |
| 6,365,659 B1 | 4/2002 | Aoyama et al. |
| 6,367,089 B2 | 4/2002 | Van Gompel et al. |
| 6,475,600 B1 | 11/2002 | Morman et al. |
| 6,537,935 B1 | 3/2003 | Seth et al. |
| 6,645,190 B1 | 11/2003 | Olson et al. |
| 6,657,009 B2 | 12/2003 | Zhou |
| 6,767,852 B2 | 7/2004 | Friderich et al. |
| 6,967,178 B2 | 11/2005 | Zhou et al. |
| 2002/0002021 A1 | 1/2002 | May et al. |
| 2002/0009940 A1 | 1/2002 | May et al. |
| 2002/0019616 A1 | 2/2002 | Thomas |
| 2002/0072561 A1 | 6/2002 | Johoji et al. |
| 2002/0081423 A1 | 6/2002 | Heffelfinger |
| 2002/0104608 A1 | 8/2002 | Welch et al. |
| 2002/0122953 A1 | 9/2002 | Zhou |
| 2002/0123538 A1 | 9/2002 | Zhou et al. |
| 2002/0123726 A1 | 9/2002 | Zhou et al. |
| 2002/0138063 A1 | 9/2002 | Kuen et al. |
| 2002/0164465 A1 | 11/2002 | Curro et al. |
| 2003/0232928 A1 | 12/2003 | Atwood et al. |
| 2004/0005832 A1 * | 1/2004 | Neculescu et al. ............ 442/149 |
| 2004/0005834 A1 | 1/2004 | Zhou et al. |
| 2004/0006324 A1 | 1/2004 | Zhou et al. |
| 2004/0127128 A1 | 7/2004 | Thomas |

FOREIGN PATENT DOCUMENTS

| | | |
|---|---|---|
| DE | 34 23 644 | 1/1986 |
| DE | 37 34 963 | 4/1988 |
| EP | 0 155 636 | 9/1985 |
| EP | 0 172 037 | 2/1986 |
| EP | 0 217 032 | 4/1987 |
| EP | 0 239 080 | 9/1987 |
| EP | 0 330 716 A2 | 9/1989 |
| EP | 0 380 781 | 8/1990 |
| EP | 0 396 800 | 11/1990 |
| EP | 0 456 885 | 11/1991 |
| EP | 0 547 497 | 6/1993 |
| EP | 0 582 569 | 2/1994 |
| EP | 0 604 731 | 7/1994 |
| EP | 0 617 939 | 10/1994 |
| EP | 0 688 550 | 12/1995 |
| EP | 0 689 815 | 1/1996 |
| EP | 0 713 546 | 5/1996 |
| EP | 0 743 052 | 11/1996 |
| EP | 0 753 292 | 1/1997 |
| EP | 0 761 193 | 3/1997 |
| EP | 0 761 194 | 3/1997 |
| EP | 0 763 353 | 3/1997 |
| EP | 0 787 474 | 8/1997 |
| EP | 0 802 251 A1 | 10/1997 |
| EP | 0 806 196 | 11/1997 |
| EP | 0 814 189 | 12/1997 |
| EP | 0 901 780 | 3/1999 |
| EP | 1 013 251 | 6/2000 |
| GB | 2 244 422 | 12/1991 |
| GB | 2 250 921 | 6/1992 |
| GB | 2 253 131 | 9/1992 |
| GB | 2 267 024 | 11/1993 |
| GB | 2 268 389 | 1/1994 |
| IS | 92891 | 2/1992 |
| JP | 3-67646 | 3/1991 |
| WO | WO 80/00676 | 4/1980 |
| WO | WO 90/03464 | 4/1990 |
| WO | WO 91/07277 | 5/1991 |
| WO | WO 92/16371 | 10/1992 |
| WO | WO 93/15247 | 8/1993 |
| WO | WO 93/17648 | 9/1993 |
| WO | WO 94/09736 | 5/1994 |
| WO | WO 95/03443 | 2/1995 |
| WO | WO 95/04182 | 2/1995 |
| WO | WO 95/16425 | 6/1995 |
| WO | WO 95/16562 | 6/1995 |
| WO | WO 95/34264 | 12/1995 |
| WO | WO 96/11236 * | 4/1996 |
| WO | WO 96/13989 | 5/1996 |
| WO | WO 96/23466 | 8/1996 |
| WO | WO 96/35402 | 11/1996 |
| WO | WO 97/17046 | 5/1997 |
| WO | WO 98/14156 | 4/1998 |
| WO | WO 98/49988 | 11/1998 |
| WO | WO 98/55062 | 12/1998 |
| WO | WO 99/17926 | 4/1999 |
| WO | WO 99/24519 | 5/1999 |
| WO | WO 99/47590 | 9/1999 |
| WO | WO 99/60969 | 12/1999 |
| WO | WO 99/60970 | 12/1999 |
| WO | WO 99/60971 | 12/1999 |
| WO | WO 00/10500 | 3/2000 |
| WO | WO 00/29199 | 5/2000 |
| WO | WO 00/37003 | 6/2000 |
| WO | WO 00/37005 | 6/2000 |

| | | | | | | |
|---|---|---|---|---|---|---|
| WO | WO 00/37009 | 6/2000 | | WO | WO 02/053667 A2 | 7/2002 |
| WO | WO 00/37723 | 6/2000 | | WO | WO 02/053668 A2 | 7/2002 |
| WO | WO 01/00053 | 1/2001 | | WO | WO 02/060690 | 8/2002 |
| WO | WO 01/32116 | 5/2001 | | WO | WO 02/085624 A1 | 10/2002 |
| WO | WO 01/49907 | 7/2001 | | WO | WO 2004/039907 A1 | 5/2004 |
| WO | WO 01/87214 | 11/2001 | | | | |
| WO | WO 02/34184 | 5/2002 | | | | * cited by examiner |

HIGH-VISCOSITY ELASTOMERIC ADHESIVE COMPOSITION

This application is a divisional of prior application Ser. No. 10/701,259 filed 4 Nov. 2003 now U.S. Pat. No. 7,316,842 which is a continuation-in-part of U.S. patent application Ser. No. 10/187,761, filed on 2 Jul. 2002, now U.S. Pat. No. 7,316,840 entitled "Strand-Reinforced Composite Material," and naming Cristian M. Neculescu and Peiguang Zhou as inventors. The entire teachings of both application Ser. Nos. 10/701,259 and 10/187,761 are hereby incorporated by reference.

BACKGROUND OF THE INVENTION

This invention is directed to highly viscous elastomeric adhesive compositions having improved elasticity at relatively low add-on levels.

Personal care garments often include elasticized portions to create a gasket-like fit around certain openings, such as waist openings and leg openings. Laminates made from conventional elastic strands and elastic attachment adhesive are often used to create such elasticized portions.

One type of elastomeric laminate is a stretch-bonded laminate that includes elastic strands produced from an extruder and bonded to a facing sheet or sheets using a hot melt adhesive. Laminates including pre-made elastic strands can be processed online but require an elastic attachment adhesive with high add-on in order to reduce strand slippage. The cost of making stretch-bonded laminates can be relatively high due to the cost of the facing sheet or sheets, plus the cost of the elastic strands, plus the cost of the adhesive.

Another type of elastomeric laminate can be made using a vertical filament laminate-stretch-bonded laminate (VFL-SBL) process. However, the VFL-SBL process must be in off-line operation due to process complexity.

Additionally, conventional elastic strand laminates can be rough and uncomfortable. Furthermore, such laminates may cause red-marking on a wearer's skin if the fit is too tight and may result in leakage from the garment if the fit is too loose. Instead, elastic laminates made with elastomeric adhesive compositions can be used in the manufacture of such garments to avoid complicated elastic-attachment steps during the garment manufacturing process.

Elastomeric adhesive compositions are multifunctional in the sense that they function as an elastomer in a nonwoven composite while also serving as a hot melt adhesive for bonding substrates. Elastomeric adhesive compositions in the form of elastomeric adhesive films are currently recognized as suitable for use in the manufacture of personal care articles. More particularly, elastomeric adhesive compositions can be used to bond facing materials, such as spunbond, to one another while simultaneously elasticizing the resulting laminate. The resulting laminate can be used to form an elastomeric portion of an absorbent article, such as a region surrounding a waist opening and/or a leg opening. U.S. Pat. No. 6,245,050 issued to Odorzynski et al., incorporated herein by reference in its entirety in a manner consistent with the present document, discloses one such elastomeric adhesive composition applied in a disposable absorbent article. Elastomeric adhesive laminates are typically more gentle and conformable compared to conventional elastic strand laminates made from conventional elastic strands with hot melt elastic attachment adhesive.

Non-woven elastomeric adhesive laminates may require high output of adhesive add-on to achieve a tension target for product application. High add-on of the film laminate may generate a bulky, thick feel and appearance, and high cost. Furthermore, the high adhesive output requirement for the film formation would make on-line processing even more difficult due to the limitation of hot melt equipment output capacity. Additionally, high processing temperatures and relatively low viscosity are often required for use with current grid melter and drum unloader processes. More particularly, known elastomeric adhesive compositions have been limited to a viscosity of 10,000 to 30,000 cps at processing temperatures of 285 to 410 degrees Fahrenheit due to grid melt capability, or less than 70,000 cps at 350 degrees as disclosed in U.S. Pat. No. 6,245,050. High add-on requirements result in high cost, and high processing temperatures result in short pot life (material degradation).

There is a need or desire for an elastomeric adhesive composition that can be used to create elasticized portions of a personal care garment, wherein the composition maintains sufficient elasticity and can be processed at lower temperatures and applied at lower add-on levels conducive to on-line processing.

SUMMARY OF THE INVENTION

In response to the discussed difficulties and problems encountered in the prior art, a new elastomeric adhesive composition has been discovered.

The present invention is directed to elastomeric adhesive compositions, and elastomeric composite laminates incorporating such elastomeric adhesive compositions, having superior elastic and adhesion properties. The elastomeric adhesive compositions are hot-melt processable and can be formed on-line at relatively low processing temperatures, and can be applied in effective amounts at relatively low add-on levels. The elastomeric adhesive compositions suitably have a viscosity between about 100,000 and about 500,000 cps at between about 300 degrees Fahrenheit (149 degrees Celsius) and about 350 degrees Fahrenheit (177 degrees Celsius), and can be processed at about 375 degrees Fahrenheit (191 degrees Celsius) or lower on commercially-available hot melt equipment.

The elastomeric adhesive compositions of the invention are made up of a base polymer and a high softening point tackifier resin. The base polymer is suitably present in an amount between about 50% and about 75% by weight, and the high softening point tackifier is suitably present in an amount between about 20% and about 40% by weight. The compositions may also include a low softening point additive, with the low softening point additive present in an amount of between about 0% and about 20% by weight. The compositions may further include an antioxidant, with the antioxidant present in an amount of between about 0.1% and about 1.0% by weight. The tackifiers may include hydrocarbons from petroleum distillates, rosin, rosin esters, polyterpenes derived from wood, and/or polyterpenes derived from synthetic chemicals. The base polymer may include polystyrene-polyethylene-polypropylene-polystyrene (SEPS) block copolymer, styrene-isoprene-styrene (SIS) block copolymer, styrene-butadiene-styrene (SBS) block copolymer, styrene-ethylene-butylene-styrene (SEBS) block copolymer, ethylene-propylene-diene (EPDM) copolymers, and/or thermoplastic polyurethane. The compositions may also include elastomeric polymer strands incorporated therein to provide added reinforcement and elasticity.

Elastomeric composite laminates can be formed by self-adhering the elastomeric adhesive compositions to one or more layers of spunbond, film, or other facing material. The elastomeric adhesive compositions may be in the form of a plurality of extruded strands, an extruded film, a melt-blown web, a foamed web, beads, or a combination of any of these forms. Laminates including the elastomeric adhesive compositions of the invention significantly improve the rate and extent of tension decay, as well as adhesion properties of the spunbond laminates compared to spunbond laminates including conventional elastomeric adhesive compositions. Furthermore, the elastomeric composite laminates of the invention require a lower output of adhesive add-on, compared to conventional elastic strand laminates, to achieve a tension target for product application, which also results in less bulk and lower cost.

The invention also includes a method of making these elastomeric adhesive compositions and laminates. These compositions can be processed by commercially available hot melt equipment. The method includes the steps of forming a solid phase composition of the base polymer and the high softening point tackifier resin, then heating the solid phase composition to a temperature of about 375 degrees Fahrenheit (191 degrees Celsius) or lower to form a liquid phase composition. A film is then formed by extruding the liquid phase composition onto a chill roll. The film can be peeled off the chill roll while stretching the film. The film can be stretched up to about 1000% from a die, at an output of between about 50 and about 120 grams per square meter before stretching. As mentioned, elastomeric polymer strands can also be incorporated into the elastomeric adhesive compositions, or the composition film may be in the form of strands. The elastomeric adhesive composition can be self-adhered to one or more facing materials, such as a nonwoven web or film to form an elastomeric composite laminate. Tension in the laminate can be adjusted by adjusting an add-on level of the elastomeric adhesive composition, or adjusting a stretch ratio of the film or strands, or varying the diameters of the strands.

These compositions and laminates are particularly suitable for use in personal care product applications, medical garment applications, and industrial workwear garment applications.

With the foregoing in mind, it is a feature and advantage of the invention to provide elastomeric adhesive compositions and laminates having improved adhesion and elastic properties, which can be produced at a relatively low cost. The invention also includes methods of making such elastomeric compositions and laminates.

DEFINITIONS

Figure 1:
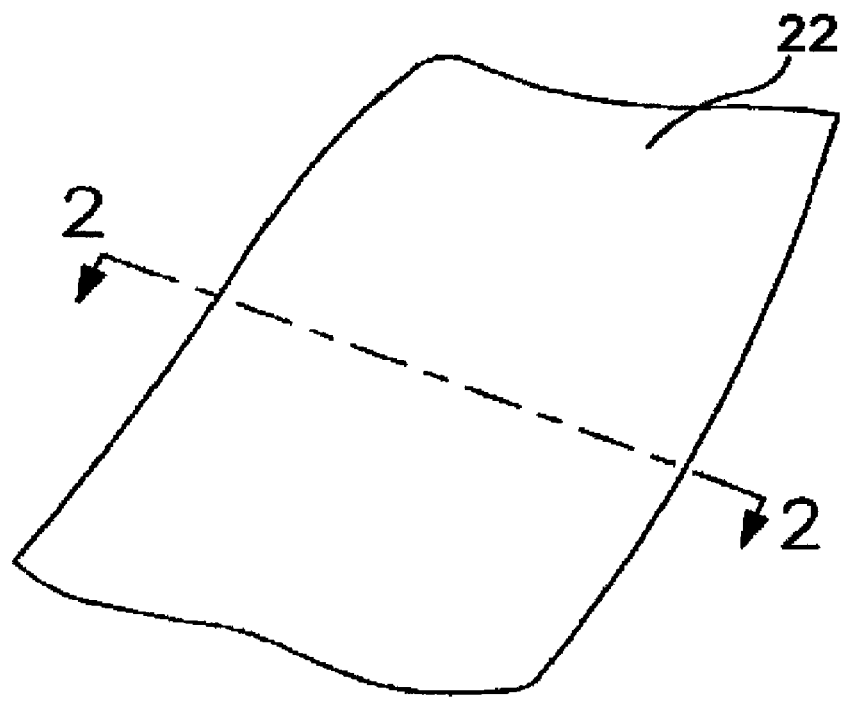
FIG. 1 is a plan view of one embodiment of an elastomeric adhesive composition of the invention.

Within the context of this specification, each term or phrase below will include the following meaning or meanings.

"Bonded" refers to the joining, adhering, connecting, attaching, or the like, of at least two elements. Two elements will be considered to be bonded together when they are bonded directly to one another or indirectly to one another, such as when each is directly bonded to intermediate elements.

"Elastic tension" refers to the amount of force per unit width required to stretch an elastic material (or a selected zone thereof) to a given percent elongation.

"Elastomeric" and "elastic" are used interchangeably to refer to a material or composite that is generally capable of recovering its shape after deformation when the deforming force is removed. Specifically, as used herein, elastic or elastomeric is meant to be that property of any material which, upon application of a biasing force, permits the material to be stretchable to a stretched biased length which is at least about 50 percent greater than its relaxed unbiased length, and that will cause the material to recover at least 40 percent of its elongation upon release of the stretching force. A hypothetical example which would satisfy this definition of an elastomeric material would be a one (1) inch sample of a material which is elongatable to at least 1.50 inches and which, upon being elongated to 1.50 inches and released, will recover to a length of less than 1.30 inches. Many elastic materials may be stretched by much more than 50 percent of their relaxed length, and many of these will recover to substantially their original relaxed length upon release of the stretching force.

"Elongation" refers to the capability of an elastic material to be stretched a certain distance, such that greater elongation refers to an elastic material capable of being stretched a greater distance than an elastic material having lower elongation.

"Film" refers to a thermoplastic film made using a film extrusion process, such as a cast film or blown film extrusion process. The term includes apertured films, slit films, and other porous films which constitute liquid transfer films, as well as films which do not transfer liquid.

"Garment" includes personal care garments, medical garments, and the like. The term "disposable garment" includes garments which are typically disposed of after 1-5 uses. The term "personal care garment" includes diapers, training pants, swim wear, absorbent underpants, adult incontinence products, feminine hygiene products, and the like. The term "medical garment" includes medical (i.e., protective and/or surgical) gowns, caps, gloves, drapes, face masks, and the like. The term "industrial workwear garment" includes laboratory coats, cover-alls, and the like.

"High softening point tackifier" refers to a tackifier having a softening point above 80 degrees Celsius, and a viscosity of at least 1500 cps at 360 degrees Fahrenheit (182 degrees Celsius) as measured by a ring and ball method (ASTM E-28).

"Layer" when used in the singular can have the dual meaning of a single element or a plurality of elements.

"Low softening point additive" refers to a tackifier or wax or low molecular weight polymers having a softening point below 80 degrees Celsius, and a viscosity of less than 1000 cps at 360 degrees Fahrenheit (182 degrees Celsius) as measured by a ring and ball method (ASTM E-28).

"Melt tank processable" refers to a composition that can be processed in conventional hot melt equipment rather than in an extruder. Hot melt equipment can be used online, such as in a diaper machine, whereas extruders are used offline due to equipment restrictions.

"Meltblown fiber" refers to fibers formed by extruding a molten thermoplastic material through a plurality of fine, usually circular, die capillaries as molten threads or filaments into converging high velocity gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al., incorporated herein by reference in its entirety in a manner consistent with the present document. Meltblown fibers are microfibers which may be continuous or discontinuous, are generally smaller than about 0.6 denier, and are generally self bonding when deposited onto a collecting surface.

"Nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Softening point" refers to a material softening temperature, typically measured by a ring and ball type method, ASTM E-28.

"Spunbond fiber" refers to small diameter fibers which are formed by extruding molten thermoplastic material as filaments from a plurality of fine capillaries of a spinnerette having a circular or other configuration, with the diameter of the extruded filaments then being rapidly reduced as taught, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein by reference in its entirety in a manner consistent with the present document. Spunbond fibers are quenched and generally not tacky when they are deposited onto a collecting surface. Spunbond fibers are generally continuous and often have average deniers larger than about 0.3, more particularly, between about 0.6 and 10.

"Strand" refers to an article of manufacture whose width is less than a film and is suitable for incorporating into a film, according to the present invention. More particularly, a strand may be thread-like with a cylindrical cross-section, for example, or may be flat or ribbon-like with a rectangular cross-section, for example.

"Thermoplastic" describes a material that softens and flows when exposed to heat and which substantially returns to a nonsoftened condition when cooled to room temperature.

"Thermoset" describes a material that is capable of becoming permanently cross-linked, and the physical form of the material cannot be changed by heat without the breakdown of chemical bonds.

"Vertical filament stretch-bonded laminate" or "VF SBL" refers to a stretch-bonded laminate made using a continuous vertical filament process, as described herein.

These terms may be defined with additional language in the remaining portions of the specification.

DESCRIPTION OF PREFERRED EMBODIMENTS

In accordance with the invention, elastomeric adhesive compositions and laminates having superior elastic and adhesion properties can be achieved using the methods described herein. The elastomeric adhesive compositions are hot-melt processable and can be formed on-line at relatively low processing temperatures, and can be applied in effective amounts at relatively low add-on levels.

The elastomeric adhesive compositions of the invention are highly viscous and have improved elasticity at lower basis weights compared to currently available elastomeric adhesive compositions. More particularly, the elastomer content of the elastomeric adhesive compositions of the invention is higher than the elastomer content of conventional elastomeric adhesive compositions, and the elastomers themselves are high moduli elastomers, thus increasing tension/add-on ratio and improving the overall elastic properties. Also, the melting temperature, or processing temperature, of the elastomeric adhesive compositions is lower, compared to conventional elastomeric adhesive compositions. By reducing the processing temperature to about 350 degrees Fahrenheit (177 degrees Celsius) or less, the pot life of the elastomeric adhesive composition is greatly improved over elastomeric adhesive compositions that are processed at higher temperatures.

These processing modifications, in comparison to conventional elastomeric adhesive compositions, result in dramatically increased viscosity. Many grid melters and drum unloaders are not equipped to handle compositions of such high viscosity, thus many manufacturers who use such hot melt equipment would not consider performing such process modifications to elastomeric adhesive compositions as described herein. However, it has been discovered that these high-viscosity elastomeric adhesive compositions can be processed on some conventional hot melt equipment, such as drum unloaders manufactured by Industrial Machine Manufacturing, Inc. of Richmond, Va., available under the trade name UNIFLOW (Models 230 and/or 2035). For example, an elastomeric adhesive composition of the invention was successfully delivered by a UNIFLOW drum unloader at 325 degrees Fahrenheit (163 degrees Celsius) with a rate of 225 pounds/hour and having a viscosity greater than 300,000 cps (assuming low shear). By using a hot-melt equipment, such as a drum unloader or and extruder, that can handle highly viscous material, such as up to about 2,000,000 cps, the formulation of the elastomeric adhesive compositions can be crafted to achieve a composition having greater elasticity at a lower add-on than conventional elastomeric adhesive compositions. Since the compositions can be applied at a lower add-on to achieve equal or greater effectiveness than conventional elastomeric adhesive compositions at higher add-on rates, the formulations of the invention thus result in cost effectiveness. In addition, the high viscosity of the formulations broadens the choice of raw materials to include more cost-effective raw materials, resulting in further overall cost effectiveness of the compositions.

Viscosity of the formulated elastomeric adhesive compositions of the invention is suitably in the range of about 100,000 to about 500,000 cps at between about 300 degrees Fahrenheit (149 degrees Celsius) and about 350 degrees Fahrenheit (177 degrees Celsius). The adhesive compositions can be processed by commercially available hot melt equipment at relatively low temperatures, such as at about 375 degrees Fahrenheit (191 degrees Celsius) or lower, or between about 325 degrees Fahrenheit (163 degrees Celsius) and about 350 degrees Fahrenheit (177 degrees Celsius). These highly viscous elastomeric adhesive compositions can be processed either directly on a converting machine or in an off-line nonwoven laminate process.

The elastomeric adhesive compositions of the invention include a base polymer and a high softening point tackifier resin. The compositions may also include a low softening point additive and/or an antioxidant. The choice of polymer and tackifier is important, as is the ratio of polymer or copolymers to tackifier. Another important consideration is the ratio of low softening point additive to high softening point tackifier.

Suitably, the composition includes the base polymer in an amount between about 50% and about 75% by weight of the composition. The base polymer suitably has a styrene content of between about 10% and about 45%, or between about 18% and about 30%, by weight of the base polymer. The base polymer may achieve the styrene content either by blending different polymers having different styrene co-monomer levels or by including a single base polymer that has the desired styrene co-monomer level. Generally, the higher the styrene co-monomer level is, the higher the tension is.

The base polymer may include polystyrene-polyethylene-polypropylene-polystyrene (SEPS) block copolymer, styrene-isoprene-styrene (SIS) block copolymer, styrene-butadiene-styrene (SBS) block copolymer, styrene-ethylene-butylene-styrene (SEBS) block copolymer, ethylene-propylene-diene (EPDM) copolymers, thermoplastic polyurethane, as well as combinations of any of these. One example of a suitable SEPS copolymer is available from Kraton Polymers of Belpre, Ohio, under the trade designation KRATON® G 2760. One example of a suitable SIS copolymer is available from Dexco, a division of ExxonMobil Corporation, under the trade designation VECTOR™.

The base polymer suitably has a Shore A hardness of between about 20 and about 90, or between about 30 and about 80. Shore A hardness is a measure of softness, and can be measured according to ASTM D-5.

In one embodiment of the invention, the base polymer may have a melt flow rate between about 5 and about 200 grams per minute, Shore A hardness between about 20 and about 70, and may be stretched up to about 1300%.

The tackifier may include hydrocarbons from petroleum distillates, rosin, rosin esters, polyterpenes derived from wood, polyterpenes derived from synthetic chemicals, as well as combinations of any of these. A key element of the compositions of the invention is a high softening point tackifier. An example of a suitable high softening point tackifier is available from Hercules Inc. of Wilmington, Del., under the trade designation PICOLYTE™ S115. Suitably, the composition includes the high softening point tackifier in an amount between about 20% and about 40% by weight of the composition.

A low softening point additive may be included in the compositions as well. A low softening point additive typically has a softening point or about 60 degrees Celsius or less and a viscosity of about 1000 cps or less at 360 degrees Fahrenheit (182 degrees Celsius), while a high softening point tackifier typically has a softening point of about 80 degrees Celsius or greater and a viscosity of about 1500 cps or greater at 360 degrees Fahrenheit (182 degrees Celsius). The use of predominantly high softening point tackifiers with high viscosity is important for adhesion improvement due to enhanced cohesive strength. However, the inclusion of relatively low amounts of low softening point additives provides instantaneous surface tackiness and pressure sensitive characteristics as well as reduced melt viscosity. Suitably, the low softening point additive is present in the composition in an amount between about 0% and about 20% by weight of the composition. One example of a particularly suitable low softening point additive is PICOLYTE™ S25 tackifier, available from Hercules Inc., having a softening point in a range around 25 degrees Celsius, or paraffin wax having a melting point of about 65 degrees Celsius may also be used.

Additionally, an antioxidant may be included in the composition, suitably in an amount between about 0.1% and about 1.0% by weight of the composition. One example of a suitable antioxidant is available from Ciba Specialty Chemicals under the trade designation IRGANOX™ 1010.

The formulated elastomeric adhesive composition suitably has an elongation-to-break of between about 500% and about 1300%, or between about 600% and about 1200%. The elongation-to-break is the point of elongation at which the composition can handle no further elongation and breaks as a result.

Figure 2:
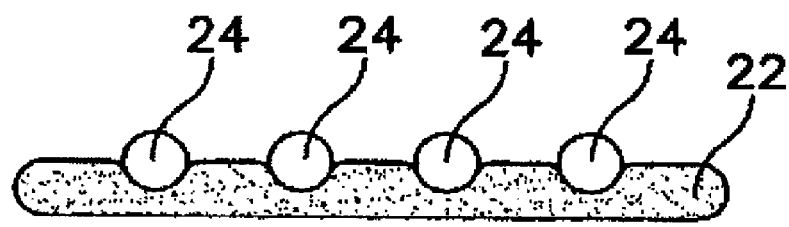
FIG. 2 is a cross-sectional view, taken along line 2-2 of FIG. 1, of another embodiment of an elastomeric adhesive composition of the invention.

One embodiment of an elastomeric adhesive composition 22 of the invention is shown in FIG. 1. In another embodiment of the invention, shown in FIG. 2 as a cross-sectional view of FIG. 1, elastomeric polymer strands 24 can be adhered to and partially embedded in the elastomeric adhesive composition 22 to further enhance laminate tension control. It will be appreciated that the elastomeric polymer strands 24 may be laid out periodically, non-periodically, and in various spacings, groupings, sizes, and compositions of elastic material according to the effect desired from the elastomeric adhesive composition 22 and the use to which it is put.

Materials suitable for use in preparing the elastomeric polymer strands 24 include diblock, triblock, tetrablock, or other multi-block elastomeric copolymers such as olefinic copolymers, including styrene-isoprene-styrene, styrene-butadiene-styrene, styrene-ethylene/butylenes-styrene, or styrene-ethylene/propylene-styrene, which may be obtained from Kraton Polymers, under the trade designation KRATON® elastomeric resin; polyurethanes, including those available from E. I. Du Pont de Nemours Co., under the trade name LYCRA® polyurethane; polyamides, including polyether block amides available from Ato Chemical Company, under the trade name PEBAX® polyether block amide; polyesters, such as those available from E. I. Du Pont de Nemours Co., under the trade name HYTREL® polyester; and single-site or metallocene-catalyzed polyolefins having density of about 0.89 grams/cubic centimeter or less, available from Dow Chemical Co. under the trade name AFFINITY®.

A number of block copolymers can also be used to prepare the elastomeric polymer strands 24 used in this invention. Such block copolymers generally include an elastomeric midblock portion B and a thermoplastic endblock portion A. The block copolymers may also be thermoplastic in the sense that they can be melted, formed, and resolidified several times with little or no change in physical properties (assuming a minimum of oxidative degradation). Alternatively, the elastomeric polymer strands 24 can be made of a polymer that is not thermally processable, such as LYCRA® spandex, available from E. I. Du Pont de Nemours Co., or cross-linked natural rubber in film or fiber form. Thermoset polymers and polymers such as spandex, unlike the thermoplastic polymers, once cross-linked cannot be thermally processed, but can be obtained on a spool or other form and can be stretched and applied as elastomeric polymer strands in the same manner as thermoplastic polymers. As another alternative, the elastomeric polymer strands 24 can be made of a thermoset polymer, such as AFFINITY®, available from Dow Chemical Co., that can be processed like a thermoplastic, i.e. stretched and applied, and then treated with radiation, such as electron beam radiation, gamma radiation, or UV radiation to cross-link the polymer, or use polymers that have functionality built into them such that they can be moisture-cured to cross-link the polymer, thus resulting in a polymer and the enhanced mechanical properties of a thermoset.

Endblock portion A may include a poly(vinylarene), such as polystyrene. Midblock portion B may include a substantially amorphous polyolefin such as polyisoprene, ethylene/propylene polymers, ethylene/butylenes polymers, polybutadiene, and the like, or mixtures thereof.

Suitable block copolymers useful in this invention include at least two substantially polystyrene endblock portions and at least one substantially ethylene/butylenes and isoprene or butadiene mid-block portion. A commercially available example of such a linear block copolymer is available from Kraton Polymers under the trade designation KRATON® G1657 elastomeric resin. Another suitable elastomer is KRATON® G2760.

The elastomeric polymer strands 24 may also contain blends of elastic and inelastic polymers, or of two or more elastic polymers, provided that the blend exhibits elastic properties. The elastomeric polymer strands 24 are substantially continuous in length. The elastomeric polymer strands 24 may have a circular cross-section, but may alternatively have other cross-sectional geometries such as elliptical, rectangular, triangular or multi-lobal.

In one embodiment, the elastomeric polymer strands 24 may be made of the same material as the elastomeric adhesive composition 22 but in the form of elongated, rectangular strips produced from a film extrusion die having a plurality of slotted openings.

Figure 3:
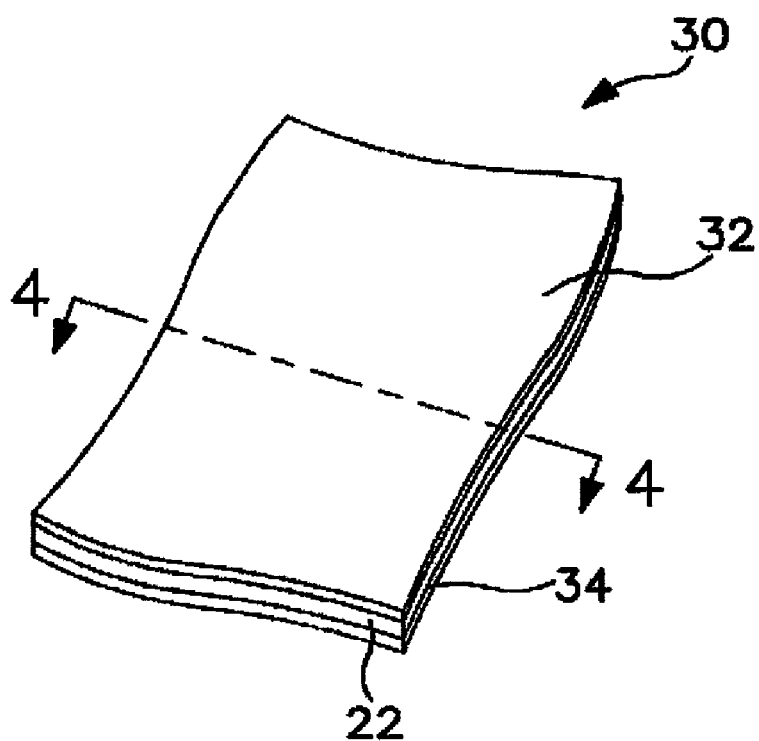
FIG. 3 is a plan view of one embodiment of an elastomeric composite laminate of the invention.
Figure 4:
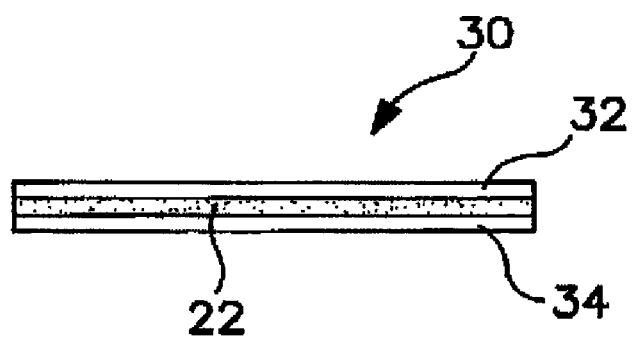
FIG. 4 is a cross-sectional view, taken along line 4-4 of FIG. 3, of an elastomeric composite laminate.

Elastomeric composite laminates 30 of the invention include the above-described elastomeric adhesive compositions 22 self-adhered to at least one facing sheet. The elastomeric adhesive compositions 22 may be applied to the facing sheet(s) at an add-on of about 120 grams/meter$^2$ (gsm) or less, or about 50 gsm or less. FIGS. 3 and 4 illustrate an elastomeric composite laminate 30 with the elastomeric adhesive composition 22 self-adhered to a first facing sheet 32 and a second facing sheet 34. The elastomeric adhesive composition 22 is capable not only of introducing a degree of elasticity to facing materials but is also capable of providing a construction adhesive function. That is, the composition 22 adheres together the facing materials or other components with which it is in contact. It is also possible that the composition 22 does not constrict upon cooling but, instead, tends to retract to approximately its original dimension after being elongated during use in a product.

Facing materials may be nonwoven webs or polymer films formed using conventional processes, including the spunbond and meltblowing processes described in the DEFINITIONS. For example, the facing sheets 32, 34 may each include a spunbonded web having a basis weight of about 0.1-4.0 ounces per square yard (osy), suitably 0.2-2.0 osy, or about 0.4-0.6 osy. The facing sheets 32, 34 may include the same or similar materials or different materials.

If the facing sheets 32, 34 are to be applied to the composition 22 without first being stretched, the facing sheets 32, 34 may or may not be capable of being stretched in at least one direction in order to produce an elasticized area. For example, the facing sheets 32, 34 could be necked, or gathered, in order to allow them to be stretched after application of the elastomeric adhesive composition 22. Various post treatments, such as treatment with grooved rolls, which alter the mechanical properties of the material, are also suitable for use. The elastomeric composite laminate 30 suitably has a basis weight between about 20 and about 120 grams per square meter.

The facing sheets 32, 34 may either be sheets of material or components, or combinations thereof. Components that may be adhered with the elastomeric adhesive composition 22 serving as a construction adhesive include elastomeric polymer strands (as described above), as well as decorative features or functional features, such as fastener material or fastening components. For example, fastener material may include hook material or loop material as used in hook-and-loop fasteners. Hook material typically includes a base or backing structure and a plurality of hook members extending outwardly from at least one surface of the backing structure. In contrast to loop material, which is typically a flexible fabric, hook material advantageously includes a resilient material to minimize unintentional disengagement of the hook members as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene, or other suitable material. Examples of commercially available hook material are available from Velcro Industries B.V., Amsterdam, Netherlands or affiliates thereof, as well as from Minnesota Mining & Manufacturing Co., St. Paul, Minn., U.S.A.

In another embodiment, the elastomeric adhesive composition 22 may be used in combination with absorbent material to form elastomeric absorbent composites. More particularly, because the elastomeric adhesive composition 22 provides adhesiveness as well as elasticity, it can be used to bond absorbent material together to form elastomeric absorbent composites. Examples of suitable absorbent material include hydrophilic fibers, such as cellulosic fluff, or a mixture of both hydrophilic and hydrophobic fibers, and/or particles of a high-absorbency material commonly known as superabsorbent material. The cellulosic fluff may be wood pulp fluff, for example. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen Inc. in Greensboro, N.C., U.S.A. Typically, a superabsorbent material is capable of absorbing at least about 10 times its weight in water, and desirably is capable of absorbing more than about 25 times its weight in water.

Figure 5:
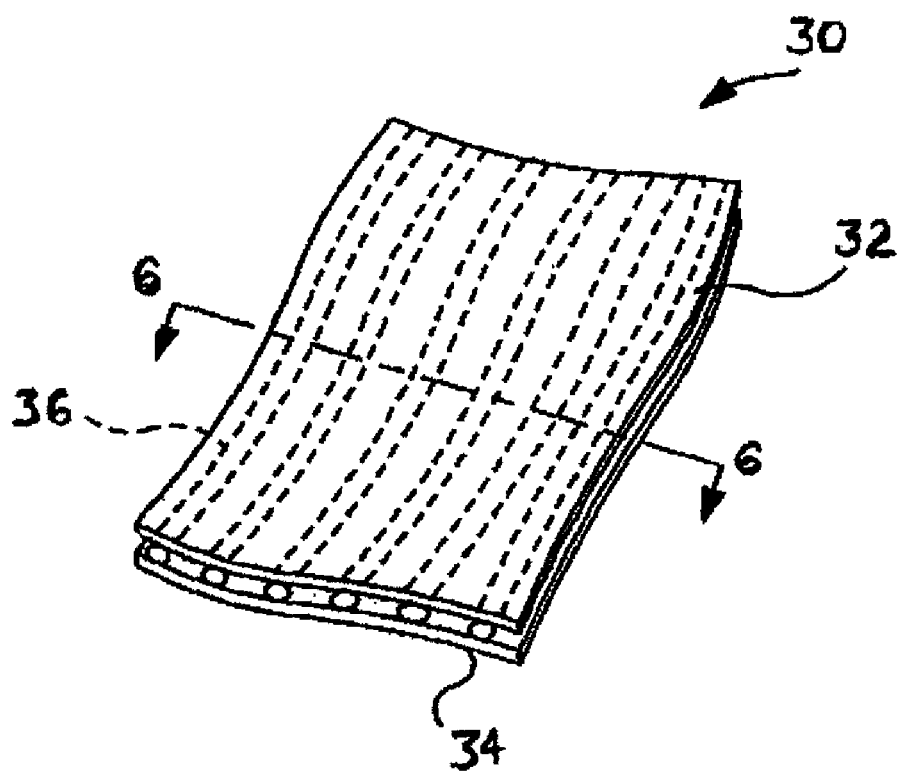
FIG. 5 is a plan view of another embodiment of an elastomeric composite laminate of the invention.
Figure 6:
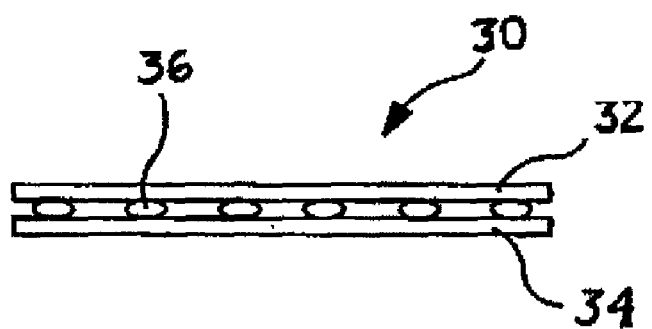
FIG. 6 is a cross-sectional view, taken along line 6-6 of FIG. 5, of an elastomeric composite laminate.

In yet another embodiment, illustrated in FIGS. 5 and 6, the elastomeric adhesive composition 22 may be in the form of a plurality of elastomeric adhesive strands 36. As shown, just like the elastomeric adhesive composition 22 in sheet form (FIGS. 3 and 4), the elastomeric adhesive strands 36 may be self-adhered to at least one facing sheet, or between a first facing sheet 32 and a second facing sheet 34. It will be appreciated that the elastomeric adhesive strands 36 may be laid out periodically, non-periodically, and in various spacings, groupings, and sizes, according to the effect desired from the elastomeric composite laminate 30 and the use to which it is put. For example, the elastomeric adhesive strands 36 may be spaced apart to between about 2 and about 20 strands per inch, or between about 5 and about 15 strands per inch.

The elastomeric adhesive strands 36 may be substantially continuous in length. The elastomeric adhesive strands 36 may have a circular cross-section, but may alternatively have other cross-sectional geometries such as elliptical, rectangular as in ribbon-like strands, triangular or multi-lobal. Each elastomeric adhesive strand 36 suitably has a diameter between about 0.05 and about 0.5 inch, or between about 0.1 and about 0.25 inch, or between about 0.15 and about 0.2 inch, with "diameter" being the widest cross-sectional dimension of the elastomeric adhesive strand.

Figure 7:
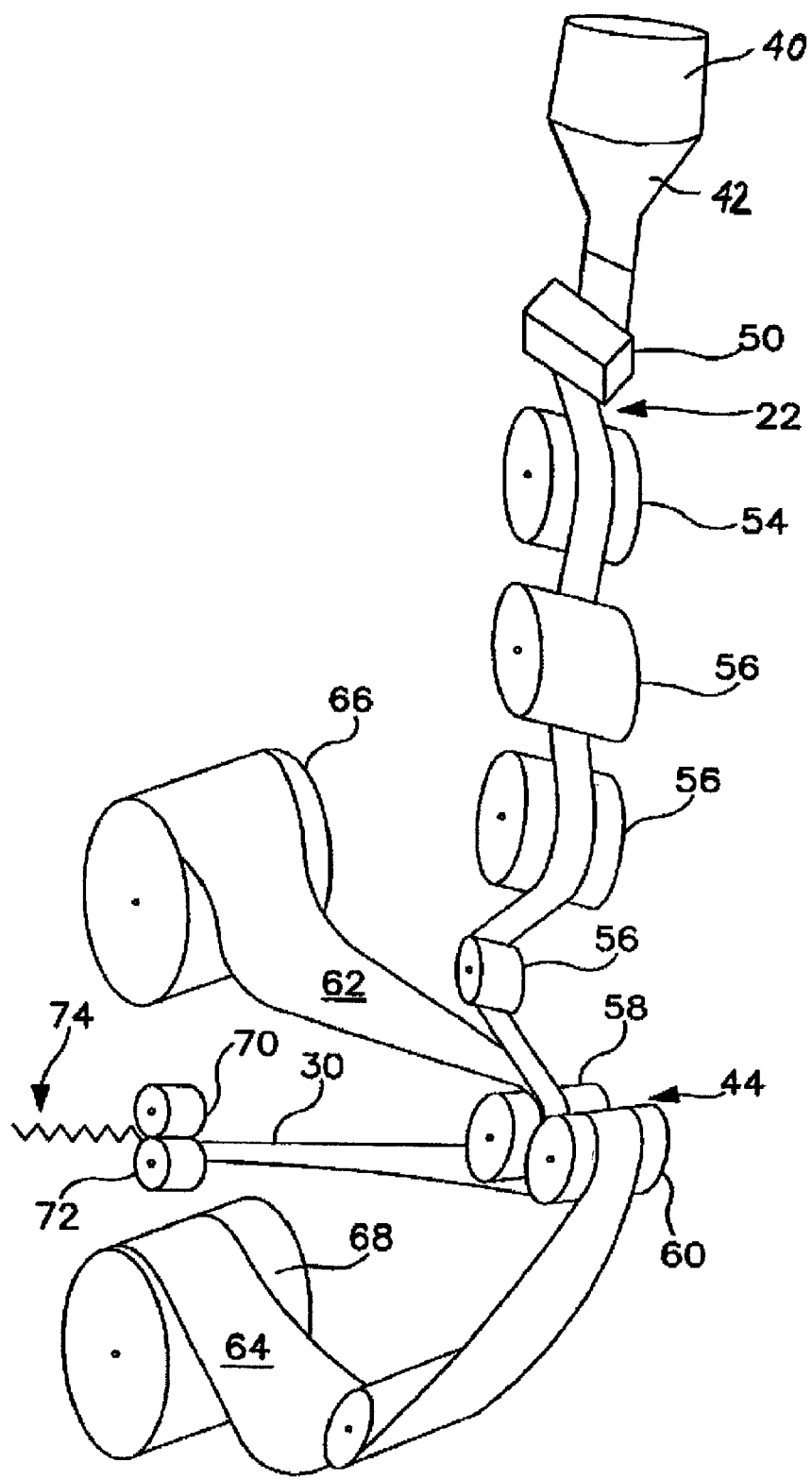
FIG. 7 illustrates a representative process for making the elastomeric adhesive compositions and laminates of the invention.

FIG. 7 illustrates a method and apparatus for making an elastomeric adhesive composition 22 and elastomeric composite laminate 30 of the invention. While FIG. 7 illustrates a composite VF SBL process it will be appreciated that other processes consistent with the present invention may be used.

The elastomeric adhesive composition 22 is formulated by mixing the base polymer and the tackifier in a Sigma blade batch mixer or by other suitable compounding methods including continuous mixing processes such as twin screw extrusion, resulting in a solid phase composition. Conventional hot melt equipment can be used to heat the composition. For example, solid blocks of the composition, or composition components, may be heated in a melt tank 40 at about 350 degrees Fahrenheit (177 degrees Celsius) or less, for example, to form a liquid phase. The liquid phase suitably has a viscosity between about 100,000 and about 500,000 cps at between about 300 degrees Fahrenheit (149 degrees Celsius) and about 350 degrees Fahrenheit (177 degrees Celsius). The highly viscous liquid phase can be processed from a drum unloader 42 through a die 50, such as a slot coat die, a strand die, a melt-blown die, or an extrusion film die, at between about 10 and about 110 grams per square meter (gsm), or between about 20 and about 80 gsm output before stretching, onto a chill roll 54 or similar device at between about 10 and about 55 degrees Celsius, for example, with the elastomeric adhesive composition 22 in the form of a film, wherein the film may be in the form of multiple elastomeric adhesive strands or a ribbon. Film output (gsm) denotes grams per square meter as measured by cutting the film with a template and weighing it. The strand(s) or ribbon may then be stretched (up to about 1000%) and thinned as the elastomeric adhesive composition 22 is peeled off the chill roll 54 and passed to one or more fly rollers 56 towards a nip 44. The film of elastomeric adhesive composition 22 may be stretched down to a narrower width and thinned by the fly rollers 56 during its passage to the nip 44. The nip 44 is formed by opposing first and second nip rollers 58, 60. Alternatively, the elastomeric adhesive composition 22 may be formed without stretching.

In an embodiment in which the elastomeric adhesive composition 22 passes through a strand die, the configuration of the strand die determines the number of elastomeric adhesive strands 36, diameter of the strands, spacing between the strands, as well as shape of the strands.

The elastomeric adhesive composition film suitably has a thickness of about 0.001 inch (0.025 mm) to about 0.05 inch (1.27 mm), alternatively of from about 0.001 inch (0.025 mm) to about 0.01 inch (0.25 mm), and a width of from about 0.05 inch (1.27 mm) to about 10 inches (25.4 cm), alternatively of from about 0.5 inch (1.27 cm) to about 5 inches (12.7 cm). The elastomeric adhesive composition film 22 may also be capable of imparting barrier properties in an application.

In order to form the elastomeric composite laminate 30, first and second rolls 66 and 68, respectively, of spunbond facing material 62, 64 or other nonwoven or film are fed into the nip 44 on either side of the elastomeric adhesive composition 22 and are self-adhered to the facing materials 62, 64. The term "self-adhered" refers to the capability of the elastomeric adhesive composition 22 to bond to a substrate by virtue of the adhesive properties present in the elastomeric adhesive composition 22. The facing materials 62, 64 might also be made in situ rather than unrolled from previously-made rolls of material. While illustrated as having two lightweight gatherable spunbond facings 62, 64, it will be appreciated that only one facing material, or various types of facing materials, may be used. The elastomeric composite laminate 30 can be maintained in a stretched condition by a pair of tensioning rollers 70, 72 downstream of the nip 44 and then relaxed as at Ref. No. 74 (FIG. 7).

When the elastomeric adhesive composition 22 is in the form of elastomeric adhesive strands 36, tension within the elastomeric composite laminate 30 may be controlled through varying the percentage stretch, or stretch ratio, of the elastomeric adhesive strands 36 prior to adhesion to the facing sheet(s), and/or through the amount of strand add-on or thickness, with greater stretch and greater add-on or thickness each resulting in higher tension. Tension can also be controlled through selection of the elastomeric adhesive composition 22, and/or by varying strand geometries and/or spacing between strands. For example, holes in the strand die through which the composition passes to form strands may vary in diameter to create elastomeric adhesive strands 36 of varied geometries.

Alternatively, the elastomeric adhesive composition 22 need not pass onto a chill roll, but instead can be applied directly from the hot-melt equipment onto the facing material(s) 62, 64. Additionally, the elastomeric adhesive composition 22 may be in the form of beads, melt-blown web, foamed web, applied in a swirl pattern, or in any other suitable adhesive form.

The elastomeric adhesive composition 22 incorporated into an elastomeric composite laminate 30 suitably has an elongation of about 50 percent or greater, alternatively of about 150 percent or greater, alternatively of from about 50 percent to about 500 percent, and a tension force of about 400 grams force per inch (2.54 cm) width or less, alternatively of about 275 grams force per inch (2.54 cm) width or less, alternatively of from about 100 grams force per inch (2.54 cm) width to about 250 grams force per inch (2.54 cm) width. Tension force, as used herein, is determined one minute after stretching the elastomeric composite laminate 30 to 100% elongation.

The elastomeric adhesive compositions 22 and elastomeric composite laminates 30 of the invention can be incorporated into any suitable article, such as personal care garments, medical garments, and industrial workwear garments. More particularly, the elastomeric adhesive compositions 22 and elastomeric composite laminates 30 are suitable for use in diapers, training pants, swim wear, absorbent underpants, adult incontinence products, feminine hygiene products, protective medical gowns, surgical medical gowns, caps, gloves, drapes, face masks, laboratory coats, and coveralls.

A number of elastomeric components are known for use in the design and manufacture of such articles. For example, disposable absorbent articles are known to contain elasticized leg cuffs, elasticized waist portions, and elasticized fastening tabs. The elastomeric adhesive compositions 22 and elastomeric composite laminates 30 of this invention may be applied to any suitable article to form such elasticized areas, or any other elasticized areas.

Figure 8:
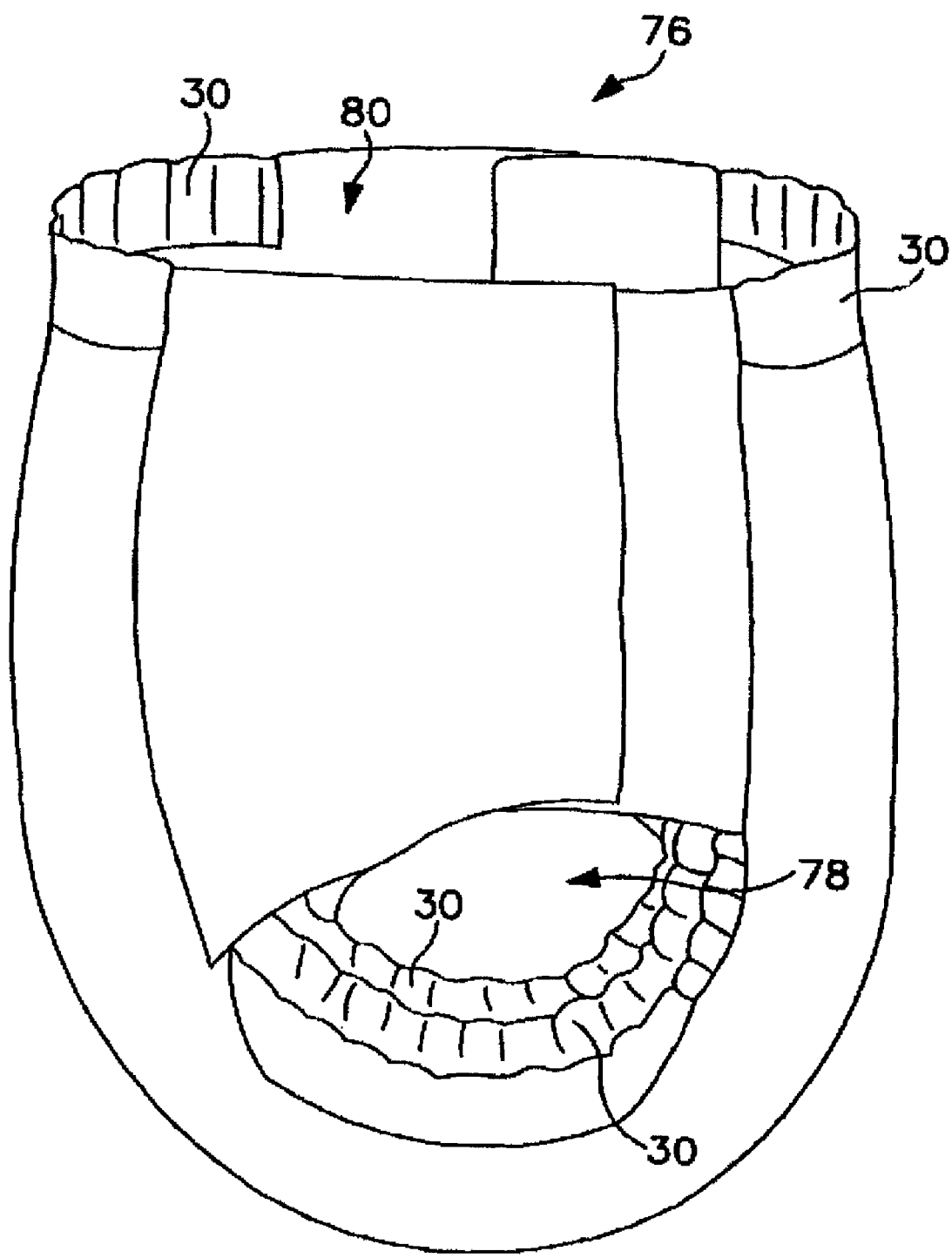
FIG. 8 is a perspective view of a garment having an elastomeric composite laminate around the leg openings and waist opening.

One example of the elastomeric adhesive compositions 22 and elastomeric composite laminates 30 incorporated into a personal care absorbent garment 76, is shown in FIG. 8. More specifically, as shown in FIG. 8, the elastomeric composite laminates 30 are particularly suitable for use in providing a gasket-like fit around leg openings 78 and waist openings 80. The elastomeric composite laminates 30 of this invention are less likely to undergo tension decay or delamination compared to similar laminates incorporating current commercial elastomeric adhesive compositions.

EXAMPLE

In this example, an elastomeric adhesive composition was formed from 54.5 wt % DPX 578 SIS copolymer and 10 wt % VECTOR 4211 SIS copolymer; both available from ExxonMobil Corporation; 35 wt % ESCOREZ 5430 tackifier, also available from ExxonMobil Corporation; and 0.50% IRGANOX 1010 antioxidant, available from Ciba Specialty Chemicals. The composition was formulated in a twin screw extruder and filled into a 58-gallon silicone lined fiber drum. Brookfield viscosity of the composition was about 145,000 cps at 380 degrees Fahrenheit (193 degrees Celsius) and about 300,000 cps at 325 degrees Fahrenheit (163 degrees Celsius). The formulation was then pumped from the fiber drum through a 1.5-inch diameter 50-foot long heated hose to adhesive head using a UNIflow model 230 drum unloader, available from Industrial Machine Manufacturing, Inc., Richmond, Va., having a 13-ton hydraulic ram powered long finger type gear pump. The temperature of the material at the adhesive head was measured at 325 degrees Fahrenheit (163 degrees Celsius). The elastomeric adhesive composition was highly elastic and exhibited sufficient adhesive properties for adhering to various substrates such as polymeric films, nonwoven webs, as well as absorbent materials, for example, superabsorbent particles, cellulose fibers, and the like.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. An elastomeric adhesive composition, comprising:
a base polymer; and
a high softening point tackifier resin having a softening point of about 80 degrees Celsius or greater, and a viscosity of about 1500 cps or greater at 182 degrees Celsius;
wherein the elastomeric adhesive composition has a viscosity between about 100,000 and about 500,000 cps at between about 149 and about 177 degrees Celsius; and
wherein the elastomeric adhesive composition further comprises an absorbent material
wherein the absorbent material comprises hydrophilic fibers, combinations of hydrophilic and hydrophobic fibers, or a super-absorbent material selected from the group consisting of natural polymers, synthetic polymer, modified natural polymers, and combinations thereof.

2. The composition of claim 1, wherein the base polymer is present in the composition in an amount between about 50% and about 75% by weight.

3. The composition of claim 1, wherein the base polymer comprises a styrene content of between about 10% and about 45% by weight.

4. The composition of claim 1, wherein the base polymer comprises at least one of the group consisting of polystyrene-polyethylene-polypropylene-polystyrene (SEPS) block copolymer, styrene-isoprene-styrene (SIS) block copolymer, styrene-butadiene-styrene (SBS) block copolymer, styrene-ethylene-butylene-styrene (SEBS) block copolymer, ethylene-propylene-diene (EPDM) copolymers, thermoplastic polyurethane, and combinations thereof.

5. The composition of claim 1, wherein the high softening point tackifier is present in the composition in an amount between about 20% and about 40% by weight.

6. The composition of claim 1, wherein the high softening point tackifier comprises at least one type of hydrocarbon selected from the group consisting of petroleum distillates, rosin, rosin esters, polyterpenes derived from wood, polyterpenes derived from synthetic chemicals, and combinations thereof.

7. The composition of claim 1, further comprising a low softening point additive having a softening point of about 60 degrees Celsius or less and a viscosity of about 1000 cps or less at 182 degrees Celsius, present in an amount between about 0% and about 20% by weight.

8. The composition of claim 1, wherein the composition is formed as at least one of the group consisting of: a plurality of extruded strands, an extruded film, a foam, a plurality of beads, and combinations thereof.

9. The composition of claim 1, wherein the composition is formed as a combination of a plurality of extruded strands and an extruded film.

10. The composition of claim 1, wherein the adhesive composition has an elongation-to-break of about 500% to about 1300%.

11. The composition of claim 1, wherein the base polymer has a styrene content of between about 10% and about 45% by weight.

12. The composition of claim 1, wherein the base polymer has a Shore A hardness of about 20 to about 90.

13. The composition of claim 1, wherein the base polymer is selected from the group consisting of elastomeric polymer compositions, tackified polymers, olefinic copolymers, ethylene-propylene-diene monomer, styrene-isoprene-styrene, styrene-butadiene-styrene, styrene-ethylene/butylene-styrene, styrene-ethylene/propylene-styrene, polyurethane, polyisoprene, cross-linked polybutadiene, and combinations thereof.

14. The composition of claim 13, wherein the high softening point tackifier resin is selected from the group consisting of petroleum distillates, rosin, rosin esters, polyterpenes derived from wood, polyterpenes derived from synthetic chemicals, and combinations thereof.

15. An elastomeric adhesive composition, comprising:
a base polymer, present in an amount between about 40% and about 80% by weight;
a high softening point tackifier resin having a softening point of about 80 degrees Celsius or greater, and a viscosity of about 1500 cps or greater at 182 degrees Celsius, present in an amount between about 20% and about 40% by weight; and
a low softening point additive having a softening point of about 60 degrees Celsius or less and a viscosity of about 1000 cps or less at 182 degrees Celsius, present in an amount between about 0% and about 20% by weight;
wherein the elastomeric adhesive composition has a viscosity between about 100,000 and about 500,000 cps at between about 149 and about 177 degrees Celsius; and
wherein the elastomeric adhesive composition further comprises an absorbent material.

16. The composition of claim 15, wherein:
the base polymer is selected from the group consisting of elastomeric polymer compositions, tackified polymers, olefinic copolymers, ethylene-propylene-diene monomer, styrene-isoprene-styrene, styrene-butadiene-styrene, styrene-ethylene/butylene-styrene, styrene-ethylene/propylene-styrene, polyurethane, polyisoprene, cross-linked polybutadiene, and combinations thereof and the high softening point tackifier resin is selected from the group consisting of petroleum distillates, rosin, rosin esters, polyterpenes derived from wood, polyterpenes derived from synthetic chemicals, and combinations thereof.

17. A method of making an elastomeric adhesive composition, comprising the steps of:
forming a solid phase composition of a base polymer and a high softening point tackifier resin having a softening point of about 80 degrees Celsius or greater and a viscosity of about 1500 cps or greater at 182 degrees Celsius;
forming a liquid phase composition by heating the solid phase composition to a temperature of about 191 degrees Celsius or lower;
achieving a viscosity of the liquid phase composition between about 100,000 and about 500,000 cps at between about 149 and about 177 degrees Celsius; and
forming an elastomeric adhesive composition by extruding the liquid phase composition through hot-melt equipment; and
incorporating an absorbent material into the elastomeric adhesive composition.

18. The composition of claim 1, wherein the absorbent material comprises hydrophilic fibers or combinations of hydrophilic and hydrophobic fibers.

19. The composition of claim 1, wherein the absorbent material comprises superabsorbent material from the group consisting of natural polymers, synthetic polymers, modified natural polymers and combinations thereof.

* * * * *